United States Patent [19]
Lang et al.

[11] Patent Number: 5,364,414
[45] Date of Patent: Nov. 15, 1994

[54] TINCTORIAL COMPOSITION FOR KERATINOUS FIBRES CONTAINING OXIDATION DYE PRECURSORS AND AMINOINDOLE COUPLERS, METHODS FOR DYEING USING THESE COMPOSITIONS AND NEW COMPOUNDS

[75] Inventors: Gerard Lang, Saint-Gratien; Alex Junino, Livry-Gargan; Jean Cotteret, Verneuil-sur-Seine; Jean J. Vandenbossche, Aulnay-sous-Bois, all of France

[73] Assignee: L'Oreal, Paris, France

[21] Appl. No.: 916,706

[22] Filed: Jul. 22, 1992

Related U.S. Application Data

[63] Continuation of Ser. No. 599,808, Oct. 22, 1990, abandoned.

[30] Foreign Application Priority Data

Oct. 20, 1989 [LU] Luxembourg .................. 87611

[51] Int. Cl.$^5$ ............................................... A61K 7/13
[52] U.S. Cl. ............................................... 8/409; 8/405; 8/406; 8/407; 8/408; 8/410; 8/423
[58] Field of Search .................. 8/405, 406, 408, 409, 8/410, 423, 428, 429, 435, 414, 416; 424/70

[56] References Cited

U.S. PATENT DOCUMENTS

| | | | |
|---|---|---|---|
| 3,630,655 | 10/1968 | Berth et al. ............... | 8/409 |
| 4,013,404 | 3/1977 | Parent et al. ............... | 8/423 |
| 4,289,495 | 9/1981 | Bugaut et al. ............... | 8/408 |
| 4,425,132 | 1/1984 | Grollier et al. ............... | 8/405 |
| 4,566,875 | 1/1986 | Grollier et al. ............... | 8/408 |
| 4,932,977 | 6/1990 | Schultz ............... | 8/408 |

FOREIGN PATENT DOCUMENTS 0186367 7/1986 European Pat. Off. .
0271186 6/1988 European Pat. Off. .
1916139 11/1969 Germany .

OTHER PUBLICATIONS

European Search Report of RS 85210, May 7, 1990.

Primary Examiner—Paul Lieberman
Assistant Examiner—Caroline L. Dusheck
Attorney, Agent, or Firm—Cushman, Darby & Cushman

[57] ABSTRACT

Oxidation tinctorial composition intended to be used for dyeing keratinous fibres, in particular human keratinous fibres and especially hair, characterized in that it contains, in a solvent medium appropriate for dyeing these fibres, at least one para oxidation dye precursor or at least one ortho oxidation dye precursor and at least one heterocyclic coupler corresponding to the formula (I):

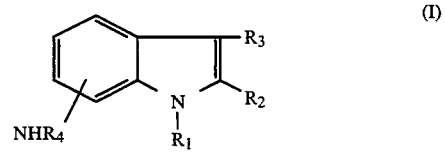

in which:

$R_1$ and $R_3$, which may be identical or different, denote a hydrogen atom or a $C_1$–$C_4$ alkyl group;

$R_2$ denotes a hydrogen atom, a $C_1$–$C_4$ alkyl group, a carboxyl group or an alkoxycarbonyl group; at least one of the radicals $R_2$ or $R_3$ denotes hydrogen;

$R_4$ denotes a hydrogen atom or a $C_1$–$C_4$ alkyl or $C_1$–$C_4$ hydroxyalkyl or $C_2$–$C_4$ polyhydroxyalkyl group;

the group $NHR_4$ occupying the positions 4, 6 or 7 of the benzene ring, as well as their salts.

20 Claims, No Drawings

TINCTORIAL COMPOSITION FOR KERATINOUS FIBRES CONTAINING OXIDATION DYE PRECURSORS AND AMINOINDOLE COUPLERS, METHODS FOR DYEING USING THESE COMPOSITIONS AND NEW COMPOUNDS

This is a continuation of application Ser. No. 07/599,808 filed Oct. 22, 1990, now abandoned The present invention relates to new tinctorial compositions for keratinous fibres and in particular for human hair, containing oxidation dye precursors and aminoindole couplers, and methods for dyeing using such compositions.

It is known to dye keratinous fibres and in particular human hair with tinctorial compositions containing oxidation dye precursors, in particular p-phenylenediamines or ortho- or para-aminophenols which are generally termed "oxidation bases".

It is also known that the hues obtained with these oxidation bases can be varied by using, in combination with these bases, couplers, also termed colouring modifiers, chosen more particularly from aromatic metadiamines, meta-aminophenols and metadiphenols.

In the field of hair dyeing, oxidation dye precursors or couplers are sought which enable a colouring having a satisfactory resistance to light, to washing, to the weather and to perspiration to be imparted to the hair, in an oxidizing alkaline medium generally used in oxidation dyeing. It is also desired to obtain colours with glints, which, in oxidation dyeing, requires the use of direct dyes stable in a reducing medium.

The Applicant has just discovered, and it is this which is the subject of the invention, that the use of certain indole derivatives as couplers, with oxidation dye precursors of the para or ortho type, enabled colours with glints having particularly surprising resistance to light, to washing, to the weather and to perspiration to be obtained after application to the keratinous fibres and in particular the hair.

One subject of the invention therefore comprises oxidation tinctorial compositions, intended to be used for dyeing keratinous fibres, containing at least one oxidation dye precursor of the para or ortho type with certain aminoindole derivatives defined below.

Another subject of the invention comprises the methods for dyeing keratinous fibres, in particular human hair, using such a composition.

Further subjects of the invention will become apparent on reading the description and the examples which follow.

The oxidation tinctorial composition according to the invention, intended to be used for dyeing keratinous fibres, in particular human keratinous fibres and especially hair, is essentially characterized in that it contains, in a solvent medium appropriate for dyeing these fibres, at least one oxidation dye precursor of the para or ortho type and at least one heterocyclic coupler corresponding to the formula (I):

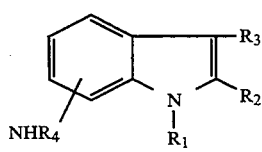

in which:
- $R_1$ and $R_3$, which may be identical or different, denote a hydrogen atom or a $C_1$–$C_4$ alkyl group;
- $R_2$ denotes a hydrogen atom, a $C_1$–$C_4$ alkyl group, a carboxyl group or an alkoxycarbonyl group; at least one of the radicals $R_2$ or $R_3$ denotes hydrogen;
- $R_4$ denotes a hydrogen atom or a $C_1$–$C_4$ alkyl or $C_1$–$C_4$ hydroxyalkyl or $C_2$–$C_4$ polyhydroxyalkyl group;
- the group $NHR_4$ occupying the positions 4, 6 or 7 of the benzene ring, as well as their salts.

Amongst the compounds of formula (I), the preferred compounds are those in which the alkyl radical denotes methyl or ethyl, the hydroxyalkyl radical denotes hydroxyethyl and the alkoxycarbonyl radical denotes methoxycarbonyl or ethoxycarbonyl.

Amongst the compounds of formula (I), those corresponding to the formula (IA) are new and this constitutes another subject of the invention.

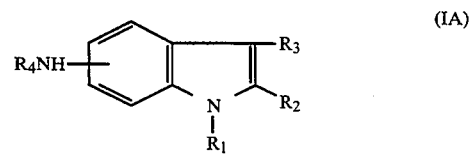

in which $R_1$, $R_2$ and $R_3$ have the meanings indicated above and $R_4$ denotes $C_1$–$C_4$ alkyl, $C_1$–$C_4$ hydroxyalkyl or $C_2$–$C_4$ polyhydroxyalkyl, $R_4NH$ occupying the positions 4, 6 or 7 and $R_4$ being other than alkyl when $R_4NH$ is in position 4.

These compounds of formula (IA) can be prepared in accordance with the following process.

The compound (IA) is obtained from the compound (IB) ($R_4=H$) by the methods for substitution of aromatic amines, in accordance with the reaction scheme:

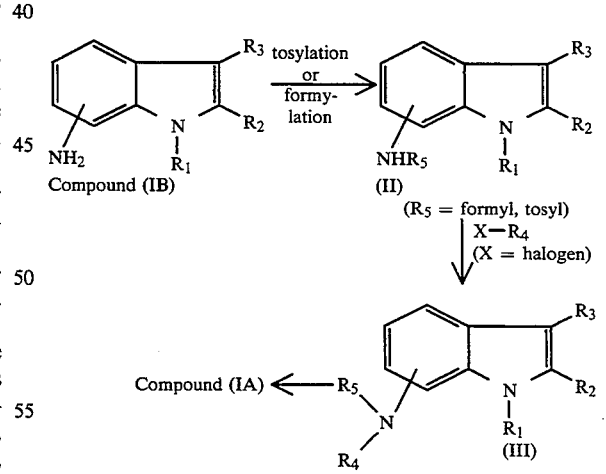

The compound (II) is obtained by formylation or tosylation. The compound (II) is subsequently alkylated by means of the alkyl halide $X$—$R_4$. When the alkyl halide is used in excess, a second group $R_4$ is introduced. The expected product (IA) is obtained by deformylation or detosylation of the compound (III) in accordance with conventional methods.

Amongst the hydroxyethylation methods, those which may be mentioned are the action of β-chloroethyl chloroformate on the compound (IB), which enables the corresponding β-chloroethyl carbamate to be obtained initially, which compound is subsequently subjected to the action of a strong inorganic base, enabling the compound (IA) for which the radical $R_4$ is a β-hydroxyethyl radical to be obtained.

Amongst the compounds of formula (I), the following may be mentioned: 6-aminoindole, 7-aminoindole, 6-N-β-hydroxyethylaminoindole, 6-N-β-hydroxyethylamino-1-methylindole, 6-methylaminoindole, 6-amino-N-methylindole, 6-amino-2-carboxyindole, 6-amino-3-methylindole, 6-amino-2-methylindole, 6-amino-2-ethoxycarbonylindole and 6-N(β,γ-dihydroxypropyl)aminoindole.

Amongst these compounds, it will be noted that, by oxidative coupling with the dye precursors defined below, 6-aminoindole and its derivatives lead to predominantly coppery hues (warm hues), and that 7-aminoindole and its derivatives lead to hues having ashy or deep auburn glints.

The dye precursors of para or ortho type are compounds which are not themselves dyes but which form dyes by an oxidative condensation process, either on themselves or in the presence of a coupler or modifier.

These dye precursors of para or ortho type are benzene or heterocyclic compounds which contain two amino groups or an amino group and a hydroxyl in the para or ortho position, the one relative to the other.

These dye precursors of para or ortho type can be chosen from paraphenylenediamines, para-aminophenols, the para heterocyclic precursors derived from pyridine or pyrimidine, such as 2,5-diaminopyridine, 2-hydroxy-5-aminopyridine and 2,4,5,6-tetraaminopyrimidine, orthoaminophenols and so-called "double" bases.

Paraphenylenediamines which may be mentioned more particularly are the compounds corresponding to the formula (II) below:

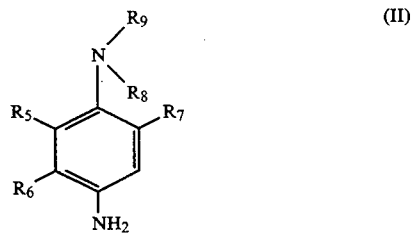
(II)

in which:

$R_5$, $R_6$ and $R_7$, which may be identical or different, represent a hydrogen or halogen atom, an alkyl radical or an alkoxy radical; and $R_8$ and $R_9$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl radical; or $R_8$ and $R_9$ form, together with the nitrogen atom to which they are bonded, a piperidino or morpholino heterocycle, with the proviso that $R_5$ or $R_7$ represents a hydrogen atom when $R_8$ and $R_9$ do not represent a hydrogen atom;
and also the salts of these compounds.

The so-called double bases are bis-phenylalkylenediamines corresponding to the formula:

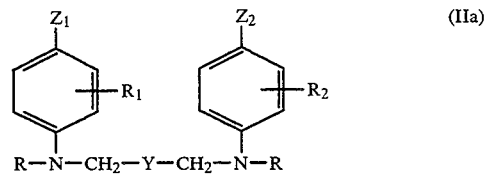
(IIa)

in which:

$Z_1$ and $Z_2$, which may be identical or different, represent hydroxyl or $NHR_3$ groups, where $R_3$ denotes a hydrogen atom or a lower alkyl radical;

$R_1$ and $R_2$, which may be identical or different, represent either hydrogen atoms or halogen atoms or alkyl groups;

R represents a hydrogen atom or an alkyl, hydroxyalkyl or aminoalkyl group, in which the amino radical can be substituted;

and Y represents a radical taken from the group comprising the following radicals: —$(CH_2)_n$—, $(CH_2)_n$, —O—$(CH_2)_n$, —, —$(CH_2)_n$, —CHOH—$(CH_2)_n$,

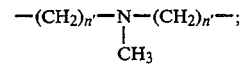

n being an integer between 0 and 8 and n' being an integer between 0 and 4, it being possible for this base to be in the form of its addition salts with acids.

The alkyl or alkoxy radicals preferably denote a group having 1 to 4 carbon atoms and in particular methyl, ethyl or propyl or methoxy or ethoxy.

Amongst the compounds of formula (II), those which may be mentioned in particular are p-phenylenediamine, p-toluylenediamine, methoxyparaphenylenediamine, 2,6-dimethyl-p-phenylenediamine, 2,5-dimethyl-p-phenylenediamine, 2-methyl-5-methoxy-paraphenylenediamine, 2,6-dimethyl-5-methoxy-p-phenylenediamine, N,N-dimethylparaphenylenediamine, 3-methyl-4-amino-N,N-diethylaniline, N,N-di(β-hydroxyethyl)paraphenylenediamine, 3-methyl-4-amino-N,N-di-(β-hydroxyethyl)aniline, 3-chloro-4-amino-N,N-di-(β-hydroxyethyl)aniline, 4-amino-N,N-(ethylcarbamylmethyl)aniline, 3-methyl-4-amino-N,N(ethylcarbamylmethyl)aniline, 4-amino-N,N-(ethyl-β-piperidinoethyl)aniline, 3-methyl-4-amino-N,N-(ethyl-β-piperidinoethyl)aniline, 4-amino-N,N-(ethyl-β-morpholinoethyl)aniline, 3-methyl-4-amino-N,N-(ethyl-β-morpholinoethyl)aniline, 4-amino-N,N-(ethyl-β-acetylaminoethyl)aniline, 4-amino-N-(β-methoxyethyl)aniline, 3-methyl-4-amino-N,N-(ethyl-β-acetylaminoethyl)aniline, 4-amino-N,N- (ethyl-β-mesylaminoethyl)aniline, 3-methyl-4-amino-N,N-(ethyl-β-mesylaminoethyl)aniline, 4-amino-N,N-(ethyl-β-sulphoethyl)aniline, 3-methyl-4-amino-N,N-(ethyl-β-sulphoethyl)aniline, N-[(4'-amino)phenyl]-morpholine and N-[(4'-amino)phenyl]piperidine. These oxidation dye precursors of para type can be introduced into the tinctorial composition either in the form of the free base or in the form of salts, such as in the hydrochloride, hydrobromide or sulphate form.

Amongst the p-aminophenols, the following may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl- 4-aminophenol, 2-(β-hydroxyethyl)-4-aminophenol, 2-methoxy-4-aminophenol, 3-methoxy-4-aminophenol and 2-methoxymethyl-4-aminophenol.

Amongst the orthoaminophenols, the following may be mentioned: 1-amino-2-hydroxybenzene, 6-methyl-1-hydroxy-2-aminobenzene and 4-methyl-1-amino-2-hydroxybenzene.

Amongst the compounds of formula (IIa), the following may be mentioned: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)-ethylenediamine, N,N'-bis(4-aminophenyl)-tetramethylenediamine, N,N'-bis(β-hydroxyethyl)-N,N'-bis(4-aminophenyl)-tetramethylenediamine, N,N'-bis(4-methylaminophenyl)-tetramethylenediamine and N,N'-bis(ethyl)-N,N'-bis(4'-amino-3'-methylphenyl)-ethylenediamine.

In addition to the heterocyclic coupler corresponding to the formula (I) above, the tinctorial compositions may also contain other couplers known per se, such as meta-diphenols, meta-aminophenols, meta-phenylenediamines, meta-acylaminophenols, meta-ureidophenols, meta-carbalcoxyaminophenols, α-naphthol and couplers having an active methylene group, such as the β-ketone compounds and the pyrazolones.

The following may be mentioned more particularly by way of example: 2,4-dihydroxyphenoxyethanol, 2,4-dihydroxyanisole, meta-aminophenol, resorcinol monomethyl ether, 2-methyl-5-aminophenol, 2-methyl-5-N-(β-hydroxyethyl)-aminophenol, 2-methyl-5-N-(β-mesylaminoethyl)-aminophenol, 2,6-dimethyl-3-aminophenol, 6-hydroxybenzomorpholine, 2,4-diaminoanisole, 2,4-diaminophenoxyethanol, 6-aminobenzomorpholine, 2-[N-(β-hydroxyethyl)-amino-4-amino]-phenoxyethanol, 2-amino-4-N-(β-hydroxyethyl)-aminoanisole, 2,4-diaminophenyl β,γ-dihydroxypropyl ether, 2,4-diaminophenoxyethylamine and their salts.

As is well known in the state of the art, direct dyes, such as azo or anthraquinone dyes or the nitro derivatives of the benzene series, may be added to these compositions.

The oxidation dye precursors of para or ortho type and the couplers used in the tinctorial compositions according to the invention preferably represent, as a whole, from 0.3 to 7% by weight relative to the total weight of the composition. The concentration of compounds (I) may vary between 0.05 and 3.5% by weight relative to the total weight of the composition.

The solvent medium appropriate for dyeing is generally aqueous and its pH may vary between 8 and 11 and is preferably between 9 and 11.

It is adjusted to the desired value with the aid of alkalinizing agents well-known in the state of the art, such as ammonia, alkali metal carbonates and alkanolamines such as mono-, di- or triethanolamine.

The tinctorial compositions according to the invention also contain, in their preferred embodiment, anionic, cationic, nonionic or amphoteric surfactants or their mixtures. Amongst these surfactants, the following may be mentioned: fatty alcohol alkylbenzenesulphonates, alkylnaphthalenesulphonates, sulphates, ethersulphates and sulphonates, quaternary ammonium salts, such as trimethylcetylammonium bromide, cetylpyridinium bromide, optionally oxyethylenated fatty acid ethanolamides, polyoxyethylenated acids, alcohols or amines, polyglycerolated alcohols, polyoxyethylenated or polyglycerolated alkylphenols and polyoxyethylenated alkyl sulphates.

These surfactants are present in the compositions according to the invention in proportions of between 0.5 and 55% by weight and preferably between 2 and 50% by weight relative to the total weight of the composition.

These compositions may also contain organic solvents to dissolve the compounds which would not be sufficiently soluble in water. Amongst these solvents, the following may be mentioned by way of example: $C_1$–$C_4$ lower alkanols, such as ethanol and isopropanol; glycerol; glycols or glycol ethers, such as 2-butoxyethanol, ethylene glycol, propylene glycol and diethylene glycol monoethyl ether and monomethyl ether, and also aromatic alcohols such as benzyl alcohol or phenoxyethanol, the analogous products or their mixtures.

The solvents are preferably present in a proportion of between 1 and 40% by weight and in particular between 5 and 30% by weight relative to the total weight of the composition.

The thickeners which may be added to the compositions according to the invention may be chosen from sodium alginate, gum arabic or guar gum, cellulose derivatives, such as methylcellulose, hydroxyethylcellulose, hydroxypropylcellulose, hydroxymethylcellulose or carboxymethylcellulose, heterobiopolysaccharides, such as xanthan gum, and the polymers derived from acrylic acid. Inorganic thickeners may also be used, such as bentonite. These thickeners are preferably present in proportions of between 0.1 and 5% and in particular between 0.2 and 3% by weight relative to the total weight of the composition.

The antioxidants which may be present in the compositions are chosen in particular from sodium sulphite, thioglycolic acid, sodium bisulphite, ascorbic acid, hydroquinonone and homogentisic acid. These antioxidants are present in the composition in proportions of between 0.05 and 1.5% by weight relative to the total weight of the composition.

These compositions may also contain other cosmetically acceptable adjuvants, such as, for example, penetration agents, sequestering agents, buffers, perfumes, etc.

The compositions according to the invention may be in various forms, such as in the form of liquids, creams or gels or in any other form appropriate for effecting a dyeing of keratinous fibres and in particular the dyeing of human hair. These compositions may be packaged in aerosol bottles in the presence of a propellant and form foams.

The tinctorial compositions according to the invention and containing an oxidation dye precursor of para and/or ortho type and a coupler of formula (I) are used in accordance with a method employing development by an oxidizing agent.

According to this method, the tinctorial composition described above is mixed at the time of use with an oxidizing solution in an amount sufficient to be able to develop a dyeing, and the mixture obtained is then applied to the keratinous fibres and in particular the human hair.

The oxidizing solution contains oxidants, such as hydrogen peroxide, urea peroxide or per salts, such as ammonium persulphate. A 20 volume hydrogen peroxide solution is preferably used.

The mixture obtained is applied to the hair and left on the hair for 10 to 40 minutes, preferably 15 to 30 minutes, after which the hair is rinsed, washed with shampoo, rinsed again and dried.

The heterocyclic coupler of formula (I) defined above can also be used in a multi-step method, consisting, in one of the steps, in applying the para and/or ortho oxidation dye precursor and, in another step, in applying the coupler of formula (I).

The oxidant be introduced, just before the application, into the composition applied in the second step, or can be added to the keratinous fibres themselves in a third step, the conditions for exposure and drying or washing being identical.

The examples which follow are intended to illustrate the invention without any restriction being implied.

PREPARATION EXAMPLE 1

Preparation of 6-N-β-hydroxyethylaminoindole

Step 1

Preparation of 6-N-(β-chloroethoxycarbonyl)aminoindole 0.05 mol (6.6 g) of 6-aminoindole and 5.5 g of calcium carbonate in 30 ml of dioxane are heated to reflux. 0.055 mol (7.9 g) of β-chloroethyl chloroformate is added little by little. The reaction mixture is diluted with ice. The expected product precipitates. It melts at 134° C.

Analysis of the product recrystallized from ethanol gives the following results:

|  | C | H | Cl | O | N |
|---|---|---|---|---|---|
| Calculated | 55.36 | 4.65 | 14.85 | 13.41 | 11.74 |
| Found | 55.40 | 4.68 | 14.72 | 13.27 | 11.67 |

Step 2

Preparation of 6-N-β-hydroxyethylaminoindole 0.28 mol (66.5 g) of 6-N-(β-chloroethoxycarbonyl)aminoindole is added to 200 ml of 4N sodium hydroxide solution and 66.5 ml of ethanol. The reaction mixture is heated under reflux for 1 hour. The expected product is precipitated by adding ice. It melts at 99° C.

Elementary analysis of the product obtained gives the following results:

|  | C | H | N | O |
|---|---|---|---|---|
| Calculated | 68.16 | 6.86 | 15.90 | 9.08 |
| Found | 67.88 | 6.91 | 15.91 | 9.15 |

PREPARATION EXAMPLE 2

Preparation of 6-N-(β-hydroxyethyl)]amino-1-methylindole hydrochloride

Step 1

Preparation of N-(6-indolyl)-1,3-oxazolidin-2-one 60 ml of methanol are added to 120 ml of a 30% solution of sodium methylate in methanol and 0.25 mol (60 g) of 6-(β-chloroethoxycarbonyl)aminoindole (prepared in accordance with the first step of Example 1) are then added, with stirring. The temperature reaches 50° C. Stirring is continued for 15 minutes after the end of the addition. The precipitate formed is drained, washed with alcohol and then dried. It melts at 199° C.

Analysis of the product recrystallized from acetic acid gives the following results:

|  | C | H | N | O |
|---|---|---|---|---|
| Calculated | 65.34 | 4.98 | 13.85 | 15.82 |
| Found | 65.42 | 5.02 | 13.75 | 15.86 |

Step 2

Preparation of N-[6-(1-methyl)indolyl]-1,3-oxazolidin-2-one 100 ml of a 30% solution of sodium methylate in methanol are added to a solution of 0.15 mol (30.5 g) of N-(6-indolyl)-1,3-oxazolidin-2-one in 300 ml of dimethylformamide. The reaction mixture is heated to 40° C. 28 ml of methyl iodide are added dropwise. Heating is continued for 1 hour after the end of the addition. After dilution of the reaction mixture with ice-water, the expected product precipitates. After draining and washing with water and then with ethanol, it melts at 160° C.

Analysis of the product recrystallized from acetic acid gives the following results:

|  | C | H | N | O |
|---|---|---|---|---|
| Calculated | 66.65 | 5.59 | 12.95 | 14.80 |
| Found | 66.55 | 5.62 | 12.76 | 15.08 |

Step 3

Preparation of 6-(β-hydroxyethyl)amino-1-methylindole hydrochloride 0.02 mol (4.32 g) of N-[6-(1-methyl)indolyl]-1,3-oxazolidin-2-one in 17 ml of 4N sodium hydroxide solution to which 2 ml of ethanol have been added is heated under reflux for 1 hour. The reaction mixture is diluted with ice-water and the product obtained is then extracted with ethyl acetate.

The oil obtained after evaporation of the ethyl acetate is added to 7 ml of a 7M hydrochloric acid solution in ethanol. The expected product precipitates.

Analysis of the product obtained after washing and drying gives the following results:

|  | C | H | Cl | N | O |
|---|---|---|---|---|---|
| Calculated | 58.28 | 6.67 | 15.64 | 12.36 | 7.06 |
| Found | 58.16 | 6.70 | 15.52 | 12.45 | 7.13 |

PREPARATION EXAMPLE 3

Preparation of 6-N-(β,γ-dihydroxypropyl)-aminoindole:

26.4 g of 6-aminoindole are dissolved in 70 ml of absolute alcohol. 29.6 g of glycidol are added and the mixture is stirred for 4 hours at 30°–40° C.

The mixture is poured into 200 g of ice-water and extracted with 3 times 100 ml of ethyl acetate. The solvent is washed with water. It is dried over $Na_2SO_4$ and driven off to dryness under vacuum.

The oily residue is taken up 3 times in 0.6 liter of isopropyl ether under reflux. The ether is filtered and driven off to dryness under vacuum; the residual oil is taken up in 10 cc of ethyl acetate and purified on a silica column (eluent ethyl acetate 9/heptane 1).

The fraction containing the expected product is evaporated to dryness under vacuum.

A colourless oil is obtained which gives the following results:

|  | C | H | N | O |
|---|---|---|---|---|
| Calculated | 64.06 | 6.84 | 13.58 | 15.51 |
| Found | 63.93 | 6.98 | 13.48 | 15.59 |

| DYES | x g |
|---|---|
| OCTYLDODECANOL sold under the name EUTANOL G by HENKEL | 8.0 g |
| OLEIC ACID | 20.0 g |
| MONOETHANOLAMINE LAURYL ETHER-SULPHATE sold under the name SIPON LM 35 by HENKEL | 3.5 g |
| ETHYL ALCOHOL | 10.0 g |
| BENZYL ALCOHOL | 10.0 g |
| CETYLSTEARYL ALCOHOL containing 33 moles of ETHYLENE OXIDE, sold under the name SIMULSOL GS by SEPPIC. | 2.4 g |
| ETHYLENEDIAMINETETRAACETIC ACID | 0.2 g |
| CATIONIC POLYMER, consisting of recurring units: | 2.2 g AS |
| MONOETHANOLAMINE | 7.5 g |
| LINOLEIC ACID DIETHANOLAMIDE sold under the name COMPERLAN F by HENKEL | 8.0 g |
| AMMONIA, containing 20% NH$_3$ | 10.2 g |
| SODIUM METABISULPHITE as a 35% aqueous solution | 1.3 g |
| HYDROQUINONE | 0.15 g |
| 1-PHENYL-3-METHYL-5-PYRAZOLONE | 0.20 g |
| DEMINERALIZED WATER | qs 100 g |

In all of the examples which follow, the compositions are mixed weight for weight with an oxidant assaying 20 volume hydrogen peroxide and having a pH of 3.

The mixtures thus produced are applied for 30 minutes to grey hair which is 90% white and the hair is then rinsed and washed. The hair is then dried.

The nature of the dyes, their amounts and the colour obtained are indicated in the tables which follow.

TABLE I

| Examples | Heterocyclic coupler | g | Para or ortho precursor | g | Colour |
|---|---|---|---|---|---|
| 1 | 6-aminoindole | 0.264 | p-phenylenediamine | 0.215 | deep coppery blond |
| 2 | 6-aminoindole | 0.528 | p-aminophenol | 0.436 | coppery golden blond |
| 3 | 6-N-β-hydroxyethyl aminoindole | 0.342 | p-phenylenediamine | 0.216 | deep coppery blond |
| 4 | 6-N-β-hydroxyethyl aminoindole | 0.684 | p-aminophenol | 0.436 | coppery golden blond |
| 5 | 7-aminoindole | 0.264 | p-phenylenediamine | 0.216 | pearly ashy blond |
| 6 | 7-aminoindole | 0.528 | p-aminophenol | 0.436 | deep auburn blond |
| 7 | 6-aminoindole | 0.264 | o-aminophenol | 0.218 | golden blond |
| 8 | 6-aminoindole | 0.264 | 2,5-diaminopyridine (dihydrochloride) | 0.364 | light coppery blond |
| 9 | 6-aminoindole | 0.264 | 2,4,5,6-tetraamino-pyrimidine sulphate monohydrate | 0.510 | light coppery golden blond |

TABLE II

| Examples | Heterocyclic coupler | g | Para or ortho precursor | g | Colour |
|---|---|---|---|---|---|
| 10 | 2-methyl-6-aminoindole | 0.292 | p-phenylenediamine | 0.215 | coppery ashy blond |
| 11 | 2-methyl-6-aminoindole | 0.585 | p-aminophenol | 0.436 | light golden blond |
| 12 | N-methyl-6-hydroxy ethylaminoindole monohydrochloride | 0.452 | p-phenylenediamine | 0.215 | iridescent deep coppery blond |
| 13 | N-methyl-6-hydroxy ethylaminoindole monohydrochloride | 0.904 | p-aminophenol | 0.436 | beige coppery blond |

Example no. 14

The following tinctorial mixture is prepared:

| p-phenylenediamine | 0.27 g |
|---|---|
| 6-N-(β,γ-dihydroxypropyl)-aminoindole | 0.52 g |
| Polyglycerolated oleyl alcohol containing 2 moles of glycerol | 4.5 g |
| Polyglycerolated oleyl alcohol containing 4 moles of glycerol | 4.5 g |
| ETHOMEEN 0 12 - ARMOON HESS CHEMICAL Ltd. (oxyethylenated oleylamine containing 12 moles of EO.) | 4.5 g |
| COMPERLAN KD - HENKEL (copra diethanolamide) | 9 g |
| Propylene glycol | 4 g |
| 2-butoxyethanol | 8 g |
| 96° ethanol | 6 g |
| MASQUOL DTPA - PROTEX (pentasodium salt of diethylenetriaminepentaacetic acid) | 2 g |
| Hydroquinone | 0.15 g |
| 35° Bé sodium bisulphite solution | 1.3 g |
| 22° Bé ammonia | 10 g |
| Water | qs 100 g |
| pH: 9.8 | |

At the time of use, 10 g of 20 volume hydrogen peroxide are added. When applied for 30 minutes at 30° C. to bleached hair, the mixture imparts a brown-red colouring to the hair after shampooing and rinsing.

We claim:

1. An oxidation tinctorial composition for dyeing keratinous fibers comprising, in a solvent medium suitable for dyeing said fibers, at least one para oxidation dye precursor, said para oxidation dye precursor being selected from the group consisting of a paraphenylenediamine, a para-aminophenol, a para heterocyclic precursor derived from an amino or hydroxy substituted pyridine or pyrimidine and a bis-phenylalkylenediamine, and at least one heterocyclic coupler having formula (I)

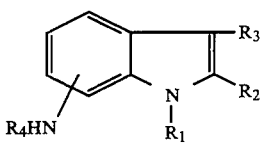

wherein $R_1$ and $R_3$, each independently, represent hydrogen or $C_1$–$C_4$ alkyl, $R_2$ represents hydrogen, $C_1$–$C_4$ alkyl, carboxyl or alkoxycarbonyl with the proviso that at least one of $R_2$ and $R_3$ represents hydrogen, $R_4$ represents hydrogen, $C_1$–$C_4$ alkyl, $C_1$–$C_4$ hydroxyalkyl or $C_2$–$C_4$ polyhydroxyalkyl; and the $NHR_4$ group occupies positions 4, 6 or 7 of the benzene ring, or a salt thereof, said heterocyclic coupler being present in an amount ranging from 0.05 to 3.5 weight percent based on the total weight of said composition and said para oxidation dye precursor and said heterocyclic coupler, as a whole, being present in an amount ranging from 0.3 to 7 percent by weight based on the total weight of said composition.

2. The composition of claim 1 wherein said paraphenylene diamine has the formula

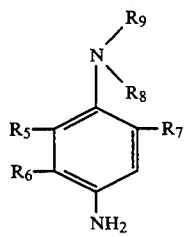

wherein $R_5$, $R_6$ and $R_7$, each independently, represent hydrogen, halogen, alkyl or alkoxy, and $R_8$ and $R_9$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, or morpholinoalkyl; or $R_8$ and $R_9$ together with the nitrogen atom to which they are attached form a piperidino or morpholino heterocycle, with the proviso that $R_5$ or $R_7$ represents hydrogen when $R_8$ and $R_9$ do not represent hydrogen; and the salts of said paraphenylene diamine.

3. The composition of claim 1 wherein said heterocyclic coupler of formula (I) is selected from the group consisting of 6-aminoindole,
7-aminoindole,
6-N-β-hydroxyethylaminoindole,
6-N-β-hydroxyethylamino-1-methylindole,
6-methylaminoindole,
6-amino-N-methylindole,
6-amino-2-carboxyindole,
6-amino-3-methylindole,
6-amino-2-methylindole,
6-amino-2-ethoxycarbonylindole and
6-N(β,γ-dihydoxypropyl)aminoindole.

4. The composition of claim 2 wherein said paraphenylene diamine is selected from the group consisting of
p-phenylenediamine,
p-toluylenediamine,
methoxyparaphenylenediamine,
2,6-dimethyl-p-phenylenediamine,
2,5-dimethyl-p-phenylenediamine,
2-methyl-5-methoxy-paraphenylenediamine,
2,6-dimethyl-5-methoxy-paraphenylenediamine,
N,N-dimethylparaphenyldiamine,
3-methyl-4-amino-N-diethylaniline,
N,N-di(β-hydroxyethyl) paraphenylenediamine,
3-methyl-4-amino-N,N-di-(β-hydroxyethyl)aniline,
3-chloro-4-amino-N,N-di-(β-hydroxyethyl) aniline,
4-amino-N,N-(ethylcarbamylmethyl) aniline,
3-methyl-4-amino-N,N-(ethylcarbamylmethyl) aniline,
4-amino-N,N-(ethyl-β-piperidinoethyl) aniline,
3-methyl-4-amino-N,N-(ethyl-β-piperidinoethyl) aniline,
4-amino-N,N-(ethyl-β-morpholinoethyl) aniline,
3-methyl-4-amino-N,N-(ethyl-β-morpholinoethyl) aniline,
4-amino-N,N-(ethyl-β-acetylaminoethyl)aniline,
4-amino-N-(β-methoxyethyl)aniline,
3-methyl-4-amino-N,N(ethyl-β-acetylaminoethyl)aniline,
4-amino-N,N-(ethyl-β-mesylaminoethyl)aniline,
4-amino-N,N-(ethyl-β-sulphoethyl)aniline,
3-methyl-4-amino-N,N-(ethyl-β-sulphoethyl)aniline,
N-[(4'-amino)phenyl]morpholine and
N-[(4'-amino)phenyl]piperidine, and the salts thereof.

5. The composition of claim 1 wherein said paraaminophenol is selected from the group consisting of
p-aminophenol,
2-methyl-4-aminophenol,
3-methyl-4-aminophenol, p0 2-chloro-4-aminophenol,
3-chloro-4-aminophenol,
2,6-dimethyl-4-aminophenol,
3,5-dimethyl-4-aminophenol,
2,3-dimethyl-4-aminophenol,
2,5-dimethyl-4-aminophenol,
2-hydroxymethyl-4-aminophenol,
2-(β-hydroxyethyl)-4-aminophenol,
2-methoxy-4-aminophenol,
3-methoxy-4-aminophenol, and
2-methoxymethyl-4-aminophenol.

6. The composition of claim 1 wherein said bisphenylalkylenediamine has the formula

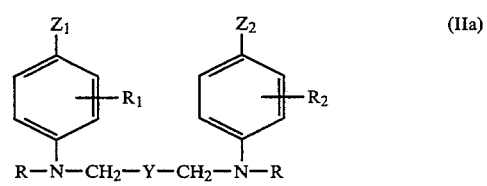

wherein $Z_1$ and $Z_2$, each independently, represent hydroxyl or $NHR_3$ wherein $R_3$ represents hydrogen or lower alkyl, $R_1$ and $R_2$, each independently, represent hydrogen, halogen or alkyl, R represents hydrogen, alkyl, hydroxyalkyl or aminoalkyl wherein the amino moiety can be substituted, and Y represents a member selected from the group consisting of —(CH$_2$)$_n$—, —(CH$_2$)$_{n'}$—O—(CH$_2$)$_{n'}$—, —(CH$_2$)$_{n'}$—CHOH—, and

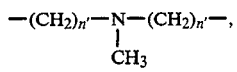

wherein
n is an integer ranging from 0 to 8, and
n' is an integer ranging from 0 to 4, and
the acid addition salt thereof.

7. The composition of claim 6 wherein said bisphenylalkylenediamine is selected from the group consisting of
N,N'-bis(β-hydroxyethyl)-N,N'-bis(4'-aminophenyl)-1,3-diaminopropan-2-ol,
N,N' -bis(β-hydroxyethyl)-N,N'-bis(4'-aminophenyl)-ethylenediamine,
N,N'-bis(4-aminophenyl)-tetramethylenediamine,
N,N'-bis(β-hydroxyethyl)-N,N'-bis(4-aminophenyl)-tetramethylenediamine,
N,N'-bis(4-methylaminophenyl)-tetramethylenediamine and
N,N'-bis(ethyl)-N,N'-bis(4'-amino-3'-methylphenyl)-ethylenediamine.

8. The composition of claim 1 wherein in addition to said heterocyclic coupler of formula (I), said composition also contains another coupler selected from the group consisting of a meta-diphenol, a meta-aminophenol, a meta-phenylenediamine, a meta-acylaminophenol, a meta-ureidophenol, a meta-carbalkoxyaminophenol, α-naphthol, a coupler having an active methylene group selected from a β-ketone compound and a pyrazolone.

9. The composition of claim 8 wherein said another coupler is selected from the group consisting of
2,4-dihydroxyphenoxyethanol,
2,4-dihydroxyanisole,
meta-aminophenol,
resorcinol monomethyl ether,
2-methyl-5-aminophenol,
2-methyl-5-N-(β-hydroxyethyl)-aminophenol,
2-methyl-5-N-(β-methylaminoethyl)aminophenol,
2,6-dimethyl-3-aminophenol,
6-hydroxybenzomorpholine,
2,4-diaminoanisole,
2,4-diaminophenoxyethanol,
6-aminobenzomorpholine,
2-[N-(β-hydroxyethyl)-amino-4-amino]-phenoxyethanol,
2-amino-4-N-(β-hydroxyethyl)-aminoanisole,
2,4-diaminophenyl β,γ-dihydroxypropyl ether,
2,4-diaminophenoxyethyl amine, and a salt thereof.

10. The composition of claim 1 which also contains a direct dye selected from the group consisting of an azo dye, an anthraquinone dye and a nitro derivative of the benzene series.

11. The composition of claim 1 wherein said solvent medium suitable for dyeing said fibers is an aqueous medium having a pH ranging from 8 to 11.

12. The composition of claim 1 which also contains at least one of an anionic, cationic or amphoteric surfactant present in an amount ranging from 0.5 to 55 weight percent based on the total weight of said composition; an organic solvent selected from a C$_1$-C$_4$ lower alkanol, glycerol, a glycol, a glycol ether or an aromatic alcohol, said organic solvent being present in an amount ranging from 1 to 40 weight percent based on the total weight of said composition; a thickener present in an amount ranging from 0.1 to 5 weight percent based on the total weight of said composition; and an antioxidant present in an amount ranging from 0.05 to 1.5 weight percent based on the total weight of said composition.

13. A method for dyeing keratinous fibers comprising applying to said fibers an oxidation tinctorial composition comprising, in a solvent medium suitable for dyeing said fibers, at least one para oxidation dye precursor, said para oxidation dye precursor being selected from the group consisting of a paraphenylenediamine, a para-aminophenol, a para heterocyclic precursor derived from an amino or hydroxy substituted pyridine or pyrimidine and a bis-phenylalkylenediamine, and at least one heterocyclic coupler having formula (I)

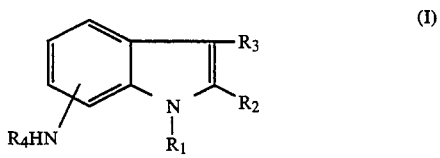

wherein
R$_1$ and R$_3$, each independently, represent hydrogen or C$_1$-C$_4$ alkyl,
R$_2$ represents hydrogen, C$_1$-C$_4$ alkyl, carboxyl or alkoxycarbonyl, with the proviso that at least one of R$_2$ and R$_3$ represents hydrogen,
R$_4$ represents hydrogen, C$_1$-C$_4$ alkyl, C$_1$-C$_4$ hydroxyalkyl or C$_2$-C$_4$ polyhydroxyalkyl,
the NHR$_4$ group occupies positions 4, 6 or 7 of the benzene ring,
or a salt thereof,
said heterocyclic coupler being present in an amount ranging from 0.05 to 3.5 weight percent based on the total weight of said composition and said para oxidation dye precursor and said heterocyclic coupler, as a whole, being present in an amount ranging from 0.3 to 7 percent by weight based on the total weight of said composition,
said precursor and coupler being mixed at the time of use with an oxidant in an amount sufficient to develop a coloring.

14. The method of claim 13 wherein the mixture of said composition and oxidant is permitted to remain in contact with said fibers for a period of time ranging from 10 to 40 minutes.

15. The method of claim 13 wherein the mixture of said composition and oxidant is permitted to remain in contact with said fibers for a period of time ranging from 15 to 30 minutes.

16. A method for dyeing keratinous fibers comprising in a first step applying to said fibers a first composition comprising at least one para oxidation dye precursor in a solvent medium suitable for dyeing said fibers, said para oxidation dye precursor being selected from the group consisting of a paraphenylenediamine, a para-aminophenol, a para heterocyclic precursor derived from an amino or hydroxy substituted pyridine or pyrimidine and a bis-phenylalkylenediamine and permitting said first composition to remain in contact with said fibers for a period of time ranging from 10 to 40 minutes, and in a second step applying to said fibers a second composition comprising in a solvent medium suitable for dyeing said fibers, at least one heterocyclic coupler having formula (I)

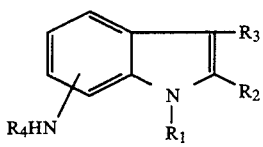

wherein
- $R_1$ and $R_3$, each independently, represent hydrogen or $C_1$-$C_4$ alkyl,
- $R_2$ represents hydrogen, $C_1$-$C_4$ alkyl, carboxyl or alkoxycarbonyl with the proviso that at least one of $R_2$ and $R_3$ represents hydrogen,
- $R_4$ represents hydrogen, $C_1$-$C_4$ alkyl, $C_1$-$C_4$ hydroxyalkyl or $C_2$-$C_4$ polyhydroxyalkyl; and
- the $NHR_4$ group occupies positions 4, 6 or 7 of the benzene ring, or a salt thereof, and permitting said second composition to remain in contact with said fibers for a period of time ranging from 10 to 40 minutes, said second composition optionally containing an oxidant in an amount effective to develop a coloring or alternatively in a third step applying to said fibers an oxidant in an amount and for a time effective to develop a coloring.

17. An oxidation tinctorial composition for dyeing keratinous fibers comprising, in a solvent medium suitable for dyeing said fibers, at least one para oxidation dye precursor, said para oxidation dye precursor being selected from the group consisting of a paraphenylenediamine, a para-aminophenol, a para heterocyclic precursor derived from an amino or hydroxy substituted pyridine or pyrimidine and a bis-phenylalkylenediamine and at least one heterocyclic coupler selected from the group consisting of 4-aminoindole, 6-aminoindole and 7-aminoindole present in an amount ranging from 0.05 to 3.5 weight percent based on the total weight of said composition and said para oxidation dye precursor and said heterocyclic precursor as a whole, being present in an amount ranging from 0.3 to 7 percent by weight based on the total weight of said composition.

18. The composition of claim 17 wherein said heterocyclic coupler is 4-aminoindole.

19. The composition of claim 17 wherein said heterocyclic coupler is 7-aminoindole.

20. An oxidation tinctorial composition for dyeing keratinous fibers comprising, in a solvent medium suitable for dyeing said fibers, at least one para oxidation dye precursor, said para oxidation dye precursor being selected from the group consisting of a paraphenylenediamine, a para-aminophenol, a para heterocyclic precursor derived from an amino hydroxy substituted pyridine or pyrimidine and a bis-phenylalkylenediamine and at least one heterocyclic coupler having formula (I)

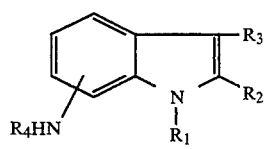

wherein
- $R_1$ and $R_3$ represent hydrogen,
- $R_2$ represents hydrogen,
- $R_4$ represents hydrogen, $C_1$-$C_4$ alkyl, $C_1$-$C_4$ hydroxyalkyl or $C_2$-$C_4$ polyhydroxyalkyl; and
- the $NHR_4$ group occupies positions 4, 6 or 7 of the benzene ring,
- or a salt thereof,
- said heterocyclic coupler being present in an amount ranging from 0.05 to 3.5 weight percent based on the total weight of said composition and said para oxidation dye precursor and said heterocyclic coupler, as a whole, being present in an amount ranging from 0.3 to 7 percent by weight based on the total weight of said composition.

* * * * *